United States Patent [19]

Farha, Jr. et al.

[11] 4,080,312
[45] Mar. 21, 1978

[54] SOLID CATALYSTS FOR OXIDATIVE DEHYDROGENATION OF ALKENES OR ALKADIENES TO FURAN COMPOUNDS

[75] Inventors: Floyd E. Farha, Jr.; Marvin M. Johnson; Donald C. Tabler, all of Bartlesville, Okla.

[73] Assignee: Phillips Petroleum Company, Bartlesville, Okla.

[21] Appl. No.: 612,513

[22] Filed: Sep. 11, 1975

Related U.S. Application Data

[62] Division of Ser. No. 380,724, Jul. 19, 1973, Pat. No. 3,912,763.

[51] Int. Cl.$^2$ .......................... B01J 27/28; B01J 23/92
[52] U.S. Cl. ..................................... 252/437; 252/435
[58] Field of Search ............................. 252/437, 435; 260/346.1 R, 346.8 A, 346.4

[56] References Cited

U.S. PATENT DOCUMENTS

| | | | |
|---|---|---|---|
| 3,230,248 | 1/1966 | Yamagita et al. | 260/530 N |
| 3,352,905 | 11/1967 | Kerr | 252/437 |
| 3,478,063 | 11/1969 | Friedrichsen et al. | 252/435 |
| 3,523,135 | 8/1970 | Asaho et al. | 260/346.4 |
| 3,697,550 | 10/1972 | Bayne et al. | 252/435 |
| 3,832,359 | 8/1974 | Freerks et al. | 252/437 |
| 3,875,220 | 4/1975 | White et al. | 252/437 |

OTHER PUBLICATIONS

Kogyo Kagaku Zasshi, Ai, 1971, 74 (z) pp. 183–186.
Chemical Abstracts, 1971, vol. 74, 125302.

*Primary Examiner*—Winston A. Douglas
*Assistant Examiner*—P. E. Konopka

[57] ABSTRACT

Alkenes and/or alkadienes are contacted with molecular oxygen and an oxidative dehydrogenation catalyst consisting essentially of phosphorus, vanadium, oxygen, and at least one promoter selected from the group consisting of iron, cobalt, nickel, and molybdenum to produce furan compounds.

6 Claims, No Drawings

SOLID CATALYSTS FOR OXIDATIVE DEHYDROGENATION OF ALKENES OR ALKADIENES TO FURAN COMPOUNDS

This is a division of copending application Ser. No. 380,724, filed July 19, 1973, now U.S. Pat. No. 3,912,763.

This invention relates to oxidative dehydrogenation catalysts and the use thereof for the conversion of alkenes and/or alkadienes to furan compounds.

Furan compounds can react readily with oxygen under oxidation conditions to produce ring cleavage and the formation of polymers. Accordingly, the production of furan compounds by the oxidative dehydrogenation of hydrocarbons has generally been avoided. Recently it has been discovered that furan compounds can be produced by the oxidative dehydrogenation of hydrocarbons in the presence of certain specific catalysts without substantial conversion of the compounds to undesirable products. The search for additional catalysts suitable for this reaction continues.

Accordingly, it is an object of the present invention to provide a new and improved oxidative dehydrogenation catalyst. Another object of the invention is to provide a new and improved process for the conversion of alkenes or alkadienes to furan compounds. Other objects, aspects, and advantages of the invention will be apparent from a study of the specification and the appended claims.

In accordance with the present invention there is provided an improved catalyst for the production of furan type compounds from unsaturated acyclic hydrocarbons having from 4 to 10 carbon atoms, which catalyst consists essentially of vanadium, phosphorus, oxygen and at least one promoter selected from the group consisting of iron, cobalt, nickel and molybdenum.

If desired, these catalysts can be supported on conventional solid catalytic support materials, for example, zinc oxide, silica, alumina, boria, magnesia, titania, zirconia, and mixtures thereof. Where a catalyst support is employed, the support will generally constitute from about 10 to about 98, preferably from about 75 to about 95, weight percent of the total catalyst composition. Supports having a surface area in the range of about 2 to about 50 $m^2/g$, preferably in the range of about 5 to about 20 $m^2/g$, are desirable. Where the promoter is iron, nickel or cobalt, the atom ratio of promoter to vanadium will generally be in the range of about 50:1 to about 2:1, and preferably will be in the range of about 5:1 to about 2:1. For the iron, nickel or cobalt promoted catalyst, the atom ratio of the total of vanadium and promoter to phosphorus will generally be in the range of about 0.3:1 to about 10:1, and preferably will be in the range of about 0.4:1 to about 6:1. The atom ratio of molybdenum to vanadium will generally be in the range of about 12:1 to about 0.1:1, preferably in the range of about 10:1 to about 0.5:1. If the catalyst composition does not contain a support material, the atom ratio of the total of vanadium and molybdenum to phosphorus will generally be in the range of about 40:1 to about 2:1, preferably in the range of about 30:1 to about 4:1. In one embodiment of the unsupported catalyst composition utilizing molybdenum, the atom ratio of molybdenum to vanadium is in the range of about 2:1 to about 8:1 and the atom ratio of the total of molybdenum and vanadium to phosphorus is in the range of about 7:1 to about 40.1. Where a solid catalyst support is utilized, the atom ratio of the total of molybdenum and vanadium to phosphorus will generally be in the range of about 7:1 to about 0.05:1, preferably in the range of about 5:2 to about 0.1:1.

The catalysts of the present invention can be prepared by many suitable techniques, for example coprecipitation, impregnation, ion exchange, aqueous or nonaqueous solution or suspension mixing or dry mixing. In general, any method can be employed which will provide a composition containing the desired elements in the defined proportions, and which has a catalytic surface area in the range of about 0.05 to about 20 $m^2/g$, preferably about 0.1 to about 5 $m^2/g$. Thus, the catalyst components and/or compounds thereof can be combined in any suitable manner. Any compound of vanadium, phosphorus or the promoter can be employed in the preparation of the catalyst so long as none of the compounds are detrimental to the final oxidative dehydrogenation catalyst and essentially all of the elements in the compounds employed, other than the vanadium, phosphorus, promoter metal and oxygen, are removed from the final catalyst by washing or by volatilization. However, small or trace amounts of some other elements which can be involved in the preparation of the catalyst can be tolerated in the final catalytic composition. For example, if alkali metal or alkaline earth metal hydroxides are employed in the preparation of the catalyst, very small residual amounts of such alkali metal and alkaline earth metals are not detrimental. Similarly, if nickel sulfate, cobalt sulfate and iron sulfate are employed in the preparation of the catalyst, small residual amounts of sulfur can be tolerated.

Generally, however, the preferred vanadium, iron, cobalt, nickel and molybdenum compounds are the oxides or phosphates of these elements or compounds which are converted to the oxide or phosphate on calcination. The preferred phosphorus compounds include the phosphorus oxides, the phosphates of the various metals employed in the catalyst as well as the ammonium phosphates; and the various forms of phosphoric acid, and admixtures thereof. Thus, suitable compounds include the oxides, phosphates, nitrates, halides, sulfates, oxalates, acetates, carbonates, propionates, tartrates, hydroxides, molybdates, vanadates, and the like, and mixtures thereof. Examples of these compounds include cobalt nitrate, cobalt acetate, cobalt hydroxide, cobalt oxide, cobalt propionate, iron oxide, iron nitrate, iron acetate, molybdenum oxide, ammonium molybdate, molybdenum phosphate, phosphoric acid, nickel oxide, nickel chloride, nickel nitrate, nickel carbonate, phosphorus pentoxide, diammonium hydrogen phosphate, cobalt phosphate, iron phosphate, nickel phosphate, vanadium oxide, vanadium phosphate, ammonium vanadate, and the like, and admixtures thereof. The term "phosphate" includes not only the monophosphate, ion, $PO_4^{-3}$, but also polyphosphate ions $(PnO_{3n+1})^{-(n+2)}$ and $[PnO_{3n-1}(OH)_2]^{-n}$ in which $n$ is an integer in the range of 2 through 100.

One technique for forming an unsupported catalyst of the present invention comprises mixing one or more phosphorus compounds, one or more vanadium compounds, and one or more promoter metal compounds.

The compounds can be admixed in the form of dry compounds and then calcined. They be admixed in the presence of a diluent to form a paste and/or one of the components can be employed in liquid form, such as phosphoric acid, to form the paste. If desired the paste can be dried before calcining. A particle forming step such as pelletizing or screening can precede the drying step or the calcining step.

A technique for forming a supported catalyst of the present invention comprises sequentially impregnating the support with solutions or dispersions of each component compound, drying and calcining the impregnated support.

The calcining step will be accomplished under conditions which ensure the conversion of any nonoxide or nonphosphate compounds to the oxide or phosphate form and the volatilizing of any elements. In general, the calcining step comprises heating the catalyst composition to a temperature in the range of about 800° F to about 1500° F for a time in the range of about 1 to about 40 hours. Presently preferred calcining conditions comprise a temperature in the range of about 850° F to about 1400° F for a time in the range of about 2 to about 24 hours in the presence of a molecular oxygen-containing gas, for example, air.

Suitable feeds for conversion to furan compounds include the acyclic alkadienes having from 4 to 10 carbon atoms. Examples include butadiene-1,3, pentadiene-1,3, isoprene, hexadiene-1,3, decadiene-1,3, and the like, and mixtures thereof. The acyclic alkadienes having from 4 to 5 carbon atoms are presently preferred. In one embodiment of the present invention, acyclic alkenes can be contacted with the defined catalyst to convert at least a portion thereof to acyclic alkadienes which can then be converted to the desired furan compounds. Examples of suitable acyclic alkenes having from 4 to 10 carbon atoms include butane-1, butene-2, n-pentene-1, isopentene, hexene-1, heptene-2, octene-1, decene-1, 2-methylbutene-1, hexene-3, 2-ethylbutene-1, 2-methylpentene-3, 3-ethylhexene-2, and mixtures thereof.

The furan compounds produced by the process of the present invention have the formula

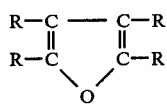

wherein each R is individually selected from the group consisting of hydrogen and alkyl radicals having from 1 to 6 carbon atoms, the total carbon atoms in the R radicals being in the range of 0 to 6. Representative products include furan, 2-methylfuran, 3-methylfuran, 2,5-diethylfuran, 2-n-hexylfuran, 2-isopropyl-3-methylfuran, 3,4-n-dipropylfuran, 3-methyl-4-n-butylfuran and the like.

In accordance with the present invention a hydrocarbon feed comprising one or more acyclic alkenes and/or one or more acyclic alkadienes is contacted, under suitable reaction conditions for conversion to furan compounds, with a molecular oxygen-containing gas in the presence of the hereinabove-defined catalyst. The molecular oxygen-containing gas can be high purity oxygen, oxygen diluted with an inert diluent such as nitrogen, flue gas containing residual oxygen, air or any other source of molecular oxygen which is at least essentially free of contaminants which would be detrimental to the desired reaction. In a presently preferred embodiment, the oxidative dehydrogenation process is carried out in the absence of any halogen. In general, the temperature will be in the range of about 500° F to about 1200° F, and preferably will be in the range of about 700° F to about 1100° F. Any suitable pressure can be employed, but, in general, the pressure will be in the range of about 0.05 to about 250 psig, and preferably will be in the range of about 0.1 to about 25 psig. The hydrocarbon feed rate will generally be in the range of about 10 to about 100 standard cubic feet of alkenes and/or alkadienes per hour per cubic foot of catalyst bed (GHSV), and preferably will be in the range of about 100 to about 500 GHSV. The mol ratio of molecular oxygen to alkenes and alkadienes will generally be in the range of about 0.1:1 to about 3:1, and preferably will be in the range of about 0.5:1 to about 2:1. Steam can be employed in the reaction zone as a diluent and heat transfer agent. When steam is utilized, the mol ratio of steam to alkenes and alkadienes will generally be in the range of about 0.1:1 to about 50:1, and preferably will be in the range of about 5:1 to about 30:1.

The alkenes, if present, are largely converted to the corresponding alkadienes. The alkadienes, in turn, are converted in significant quantities to the corresponding furan compounds. However, the reaction effluent can also contain unreacted feed material, alkenes including ethylene, propylene, and butenes, oxides of carbon, alkenylcycloolefins, crotonaldehyde, acetaldehyde, and other oxygenated products. The furan compounds can be recovered by suitable techniques, for example by condensation from the reactor gas effluent followed by distillation. Unconverted alkenes and/or alkadienes can be recovered and recycled to the reactor, as can other materials such as crotonaldehyde which are convertible to furan compounds under the reaction conditions. If desired, the conversion of alkenes to furan compounds can be conducted in two reaction zones in series. The first reaction zone can be operated under conditions favorable for the conversion of the alkenes to alkadienes, while the second reaction zone can be operated under conditions favorable to the conversion of the alkadienes to furan compounds. The effluent from the reaction zone can be subjected to conventional separation techniques to recover unconverted alkenes for recycle to the first reaction zone and a concentrated alkadiene stream for feed to the second reaction zone. If desired, the total effluent from the first reaction zone can be passed directly to the second reaction zone without separation. The effluent of the second reaction zone can be processed for recovery and recycle of unreacted alkadienes to the second reaction zone and for recovery of a furan compound product. The catalyst of the present invention can be employed in both reaction zones, or another suitable dehydrogenation catalyst can be employed in the first reaction zone while the present catalyst is utilized in the second reaction zone.

The following example is presented in further illustration of the invention and should not be construed in undue limitation thereof.

EXAMPLE

In each of a series of runs employing various catalysts, butadiene was contacted with molecular oxygen and steam in the presence of the respective catalyst. The reaction conditions and results are shown in the following table. Two cubic centimeters of the respective catalyst was employed in each run.

TABLE

| Run | Promoter | Promoter/Vanadium Atom Ratio | Atom Ratio Total Metal to Phosphorus | Temp. °F | GHSV Butadiene | O$_2$ | Steam | % Conversion Butadiene | mol % yield Furan | % Selectivity to Furan | Mol % Yield Oxygenated Products | % Selectivity Oxygenated Products |
|---|---|---|---|---|---|---|---|---|---|---|---|---|
| 1 | — | — | 3/1 | 900 | 100 | 50 | 2000 | 28.7 | 7.2 | 25.0 | 10.1 | 35.2 |
| 2 | — | — | 3/1 | 1100 | 100 | 50 | 2000 | 31.5 | 6.2 | 19.8 | 8.7 | 27.8 |
| 3 | — | — | 3/1 | 1100 | 400 | 200 | 8000 | 8.9 | 2.6 | 29.6 | 3.4 | 38.0 |
| 4 | — | — | 3/1 | 900 | 400 | 200 | 8000 | 5.2 | 1.9 | 37.0 | 2.5 | 49.0 |
| 5 | Co | 4/1 | 0.5/1 | 1000 | 400 | 400 | 8000 | 14.5 | 10.5 | 72.4 | 10.9 | 75.5 |
| 6 | Ni | 4/1 | 0.5/1 | 1000 | 400 | 400 | 8000 | 20.6 | 12.2 | 59.2 | 12.9 | 62.9 |
| 7 | Fe | 4.5/1 | 0.5/1 | 1000 | 400 | 400 | 8000 | 10.1 | 6.8 | 67.3 | 10.6 | 71.4 |
| 8 | Fe | 45/1 | 5.7/1 | 700 | 400 | 400 | 8000 | 24.1 | 6.1 | 25.3 | 7.0 | 29.2 |
| 9 | Mo | 8/1 | 13/1 | 1000 | 400 | 400 | 8000 | 24.2 | 17.2 | 71.0 | 18.1 | 74.9 |
| 10 | Mo | 8/1 | 27/1 | 1000 | 400 | 400 | 8000 | 25.5 | 16.7 | 65.5 | 18.1 | 70.9 |
| 11 | Mo | 8/1 | 7/1 | 1000 | 400 | 400 | 8000 | 13.5 | 9.9 | 73.3 | 10.3 | 75.6 |
| 12 | Mo | 2/1 | 16/1 | 900 | 400 | 400 | 8000 | 26.0 | 12.8 | 49.2 | 13.3 | 51.2 |
| 13 | Mo | 8/1 | 4.5/1 | 1000 | 400 | 400 | 8000 | 5.1 | 1.7 | 34.1 | 1.7 | 34.1 |
| 14 | Mo | 8/1 | 4.5/1 | 1000 | 400 | 400 | 8000 | 7.1 | 2.3 | 32.4 | 2.6 | 36.6 |
| 15 | Mo | 4/1 | 1.2/1 | 900 | 400 | 400 | 8000 | 16.4 | 7.9 | 48.1 | 8.1 | 49.2 |
| 16 | Mo | 4/1 | 1.2/1 | 1000 | 400 | 400 | 8000 | 4.3 | 1.3 | 30.6 | 1.3 | 30.6 |
| 17 | Mo | 8/1 | 2.2/1 | 900 | 400 | 400 | 8000 | 2.9 | 1.2 | 42.6 | 1.2 | 42.6 |
| 18 | Mo | 8/1 | 1.5/1 | 900 | 400 | 400 | 8000 | 17.4 | 7.4 | 42.5 | 7.7 | 44.5 |
| 19 | Mo | 1/1 | 2/1 | 900 | 400 | 400 | 8000 | 22.6 | 9.5 | 42.0 | 10.2 | 45.2 |
| 20 | Mo | 1/1 | 0.67/1 | 900 | 400 | 400 | 8000 | 24.0 | 9.6 | 40.0 | 10.2 | 42.4 |

The catalysts were generally prepared in small lots of about 20 grams or less using the amounts of each component required to give the atom ratios shown in the Table. The catalysts of runs 1–14 were employed without supports.

The catalyst of runs 1–4 was made by mixing together phosphorus pentoxide and vanadium pentoxide and calcining the product for 16 hours at 1000° F.

The catalysts of runs 5–8 were made by mixing together an oxide or carbonate of the promoter metal (i.e., cobalt, nickel or iron), phosphoric acid and ammonium vanadate to form a paste, evaporating the paste to dryness and calcining the product. The catalyst of run 5 was calcined 7 hours at 850° F, the catalysts of runs 6 and 7 were calcined 18 hours at 850° F, and the catalyst of run 8 was calcined at 1000° F between 6 and 12 hours.

The catalysts of runs 9–13 were made by mixing together molybdenum trioxide, phosphoric acid, water and ammonium vanadate to form a paste, evaporating the paste to dryness and calcining at 1000° F. The calcining times were 16 hours for the catalysts of runs 9–11, 6 hours for the catalyst of run 12, and 8 hours for the catalyst of run 13.

The catalyst of run 14 was made by mixing together molybdenum trioxide, phosphoric acid, water and vanadium trioxide to form a paste, evaporating the paste to dryness and calcining the product at 1000° F for 16 hours.

Supported catalysts were used in runs 15–20. The support in each instance was silica and the final composition contained about 8 weight percent catalyst and 92 weight percent silica. Each composition was made by impregnating the support with a solution formed by dissolving the requisite quantities of ammonium molybdate and ammonium vanadate in dilute phosphoric acid and evaporating the composite to dryness. The composite was calcined at 1000° F for 4 hours.

The gaseous effluents, on a dry basis, were analyzed by means of gas-liquid chromatography. Products found included unreacted butadiene, furan, acetaldehyde, carbon oxides, ethylene, propylene and butenes. The reported selectivities to furan and furan plus acetaldehyde are modified selectivities based on the above gaseous product analyses. The yields of furan and acetaldehyde are in terms of mols per 100 mols of butadiene feedstock. The oxygenated products reported in the Table are furan and acetaldehyde.

The catalysts were normally tested at reactor temperature of 700°, 800°, 900° and 1000° F in sequence. Data are reported only for those runs in which significant amounts of furan were produced.

The results show in general that promoting a vanadium/phosphorus/oxygen catalyst with a metal selected from the group consisting of cobalt, iron, nickel, and molybdenum in accordance with the invention can significantly improve the conversion of butadiene to furan and acetaldehyde, and to furan in particular. The selectivity to the oxygenated products is also, in general, improved by using the catalysts of the instant invention.

Reasonable variations and modifications are possible within the scope of the foregoing disclosure and the appended claims to the invention.

That which is claimed is:

1. A calcined unsupported catalyst composition consisting essentially of phosphorus, vanadium, oxygen and molybdenum, wherein the atom ratio of molybdenum/vanadium is about 8:1 and the atom ratio of the total of molybdenum and vanadium to phosphorus is in the range of about 40:1 to about 7:1, and wherein the calcination of the unsupported catalyst composition was conducted at a temperature in the range of about 800° F to about 1500° F for a time in the range of about 1 to about 40 hours in the presence of a molecular oxygen-containing gas.

2. A calcined unsupported catalyst composition in accordance with claim 1 wherein said composition has a catalytic surface area in the range of about 0.05 to about 20 m$^2$/g.

3. A calcined unsupported catalyst composition in accordance with claim 1 wherein said composition has a catalytic surface area in the range of about 0.1 to about 5 m$^2$/g.

4. A calcined unsupported catalyst composition consisting of phosphorus, vanadium, oxygen and molybdenum, wherein the atom ratio of molybdenum/vanadium is about 8:1 and the atom ratio of the total of molybdenum and vanadium to phosphorus is in the range of 40:1 to about 7:1, and wherein the calcination of the unsupported catalyst composition was conducted at a temperature in the range of about 800° F to about 1500° F for a time in the range of about 1 to about 40 hours in the presence of a molecular oxygen-containing gas.

5. A calcined unsupported catalyst composition in accordance with claim 4 wherein said composition has a catalytic surface area in the range of about 0.05 to about 20 $m^2/g$.

6. A calcined unsupported catalyst composition in accordance with claim 4 wherein said composition has a catalytic surface area in the range of about 0.1 to about 5 $m^2/g$.

* * * * *